United States Patent [19]

Pies et al.

[11] 4,102,205
[45] Jul. 25, 1978

[54] METHOD AND APPARATUS FOR ULTRASONIC NONDESTRUCTIVE TESTING OF WORKPIECES WITH AUTOMATIC COMPENSATION FOR THE PROBE, WORKPIECE MATERIAL, AND TEMPERATURE

[75] Inventors: Wilfried Pies, Erftstadt-Bliesheim; Reinhard Brandt, Turnich, both of Fed. Rep. of Germany

[73] Assignee: Krautkramer-Branson, Incorporated, Stratford, Conn.

[21] Appl. No.: 793,611

[22] Filed: May 4, 1977

[30] Foreign Application Priority Data

May 26, 1976 [DE] Fed. Rep. of Germany ....... 2623522

[51] Int. Cl.² ............................................. G01N 29/04
[52] U.S. Cl. ........................................ 73/626; 73/614; 73/631
[58] Field of Search .................. 73/67.5 R, 67.6, 67.7, 73/67.8 R, 67.8 S, 67.9, 626, 631

[56] References Cited

U.S. PATENT DOCUMENTS

| 3,555,889 | 1/1971 | Weighart | 73/67.9 |
| 3,942,361 | 3/1976 | Rath | 73/67.7 |
| 4,043,181 | 8/1977 | Nigam | 73/67.8 R |

*Primary Examiner*—Richard C. Queisser
*Assistant Examiner*—John P. Beauchamp
*Attorney, Agent, or Firm*—Ervin B. Steinberg; Philip J. Feig

[57] ABSTRACT

A method and apparatus for ultrasonic nondestructive testing of workpieces include automatic compensation of echo responsive electrical signals commensurate with preprogrammed test parameters. The test parameters include at least one of the following: depth dependent correction of the individual DGS (distance, gain, size) values for each respective probe; correction for material related properties of the workpiece and coupling medium; correction for temperature affecting the testing of the workpiece. Preferably, a compensating signal generated commensurate with the sum of the correction signals is used for varying either the gain of a receiver amplifier or a predetermined level provided to a comparator circuit or both. Embodiments disclosed are applicable for processing both analog and digital echo responsive electrical signals.

11 Claims, 11 Drawing Figures

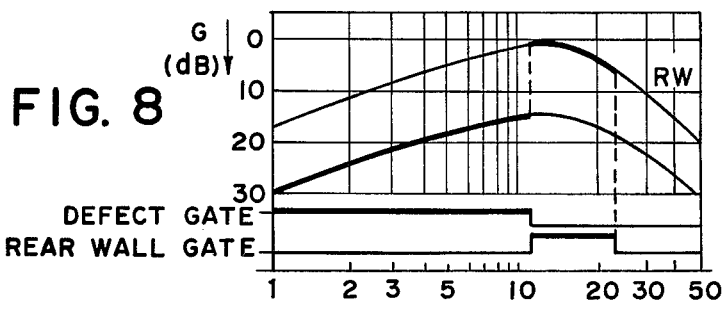
FIG. 8 — DGS DIAGRAM STORED IN PROM 15
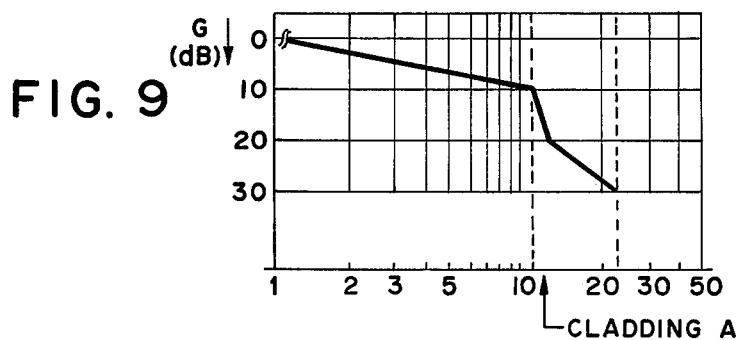
FIG. 9 — MATERIAL COEFFICIENT ACOUSTIC ATTENUATION STORED IN PROM 16
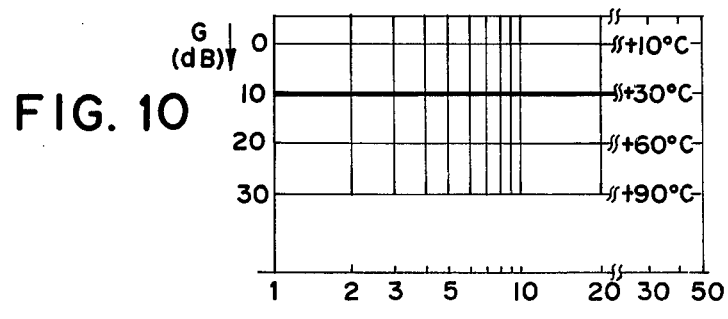
FIG. 10 — TEMPERATURE COEFF. STORED IN PROM 18
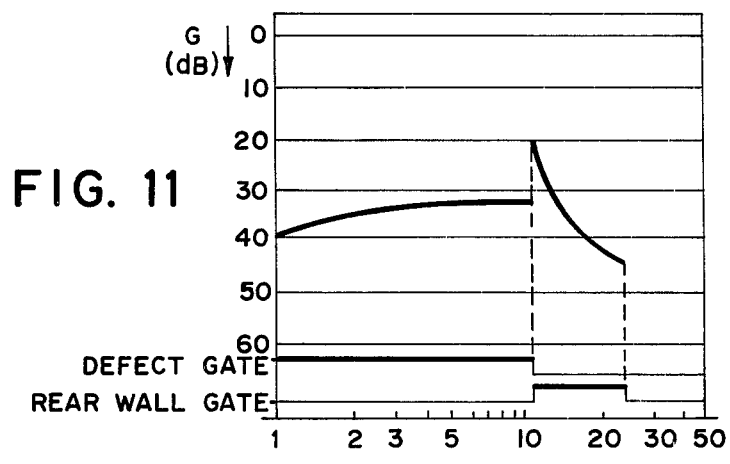
FIG. 11 — RESULTING COMPENSATION CURVE

METHOD AND APPARATUS FOR ULTRASONIC NONDESTRUCTIVE TESTING OF WORKPIECES WITH AUTOMATIC COMPENSATION FOR THE PROBE, WORKPIECE MATERIAL, AND TEMPERATURE

SUMMARY OF THE INVENTION

This invention relates to a method of and apparatus for nondestructive ultrasonic testing of workpieces, having automatic workpiece depth dependent correction of the individual DGS (distance, gain, size) values of all the respective test probes as well as providing for the correction of the material related properties of the workpiece, and of the coupling distance, or the coupling medium respectively.

Attenuation of ultrasonic signals used in ultrasonic testing of workpieces may be caused, firstly, by the chemical and physical structure (material coefficient) as well as the temperature of the workpiece and coupling medium and, secondly, by the sound beam distribution (DGS value) which is characteristic of the test probe.

It is well known that in the pulse-echo method of ultrasonically testing a workpiece the ultrasonic energy reflected at a defect or other acoustic discontinuity, i.e. the echo signal, is converted by the test probe into an electrical signal and used for defect evaluation. In the through transmission method of testing, the acoustic energy received by one or more receiver test probes is attenuated by the amount of such energy reflected at the defect and is likewise transformed by the test probe into an electrical signal and used for defect evaluation. However, reflections take place not only at a defect in the workpiece (non-homogeneity), but also at the entrant surface and at the rear wall, which latter surface appears as a defect of infinite size. The interval during which receipt of defect responsive echoes are anticipated is preferably separated from the interval during which rear wall responsive echoes are anticipated by the use of defect echo gates and rear wall echo gates respectively. By such segregation of the echo responsive signals, rear wall echoes are precluded from being mistaken as a defect in the workpiece. Since the ultrasonic signal has to be transmitted from the test probe to the workpiece through a coupling medium or delay line having a finite coupling distance through which attenuation or interference can occur, thereby raising the possibilities of erroneous signals, a positive test result can be assured only when the rear wall echo and/or a defect echo are received.

It is also known that insufficient coupling of the test probe to the workpiece can be detected by evaluating the amplitude level of the rear wall echo signal. Moreover, by comparing the rear wall echo signal amplitude level with the amplitude level of the defect echo signal occurring during the defect gate interval, the magnitude of the defect can be determined.

All ultrasonic test probes display, as is known, a defect (reflector) echo amplitude dependent upon the distance of the defect from the probe. This defect amplitude dependency can be empirically determined individually for each test probe by means of the so-called DGS (distance/gain/size of the equivalent defect) diagram. The DGS diagram gives the distance dependent relationships which are related to the shape of the ultrasonic beam and to the size of the defect. Use is made of the so-called size of the equivalent defect because it is not possible to describe the true magnitude of a defect (non-homogeneity). The representation of the value of the equivalent defect is based upon a simplified representation of the shape, position and reflection behavior of small defects in the workpiece. More precisely, the representation is based upon a flat circular disc reflector which is intercepted in its center by the main ray of the acoustic beam and causes a one-hundred percent reflection of the sonic energy, see Krautkramer, Werkstoffpruefung mit Ultraschall, 3rd edition, pp. 86 et seq, Springer Verlag, Berlin (1975) (in German language). In order to compensate for the decrease in the sensitivity of test probes as a function of the distance of the defect from the surface of the workpiece it is known to use depth compensating circuits, e.g. the three point depth compensation in which the starting point, the level and the increase of the sensitivity compensation (slope) are adjusted. Using this type of depth compensation it is not possible, however, to compensate for varying material coefficients, for instance, the different absorption values of clad workpieces. Also, it is not possible with this type of compensating circuit to compensate for temperature variations and, therefore, variations of the temperature coefficients during a test.

In another known method using only transmitter/receiver test probes, it is proposed that by evaluation of the differences of the digital peak values of the defect and rear wall echo responsive signals a standardization may be obtained by which, after the end of an individual transmitted search signal, a depth compensating function is added to the received signal. This evaluation method can only be used for pulse-echo operation, and uses the peak value of one echo signal for the coordination of the depth compensation corrections as a function of transit time although this instant of time bears no fixed relationship to the depth position of the defect. (See, German Offenlegungsschrift No. 2,226,172.)

The present invention has as its object to derive and utilize correction values having a high degree of accuracy pertaining to the test probe DGS values, material coefficients and effects of the coupling path distance. In accordance with this invention, the problem presented is solved in that the correction value of the temperature coefficient and the correction values for the depth dependent acoustic attenuation factors, such as DGS values and material coefficients are continuously recalled from storage means and are summed in a digital adder to form a combined correction value for each test probe. These correction values can be fed to an amplifier as a compensating signal.

A modified arrangement provides that the compensating signals are fed to a gate (comparator) which evaluates the amplitude of the echo signal. In a further modified arrangement, the correction values are fed to both the amplifier and the gate.

Correction of the test probe DGS values preferably is made for standard test probes as well as for transmitter/receiver test probes both for the region of a small reflector (defect) and for the region of an infinitely large reflector (rear wall) detection. Moreover, the material coefficient and temperature coefficient values can be used not only in pulse-echo testing but also in through transmission testing.

The invention will become more clearly apparent when the following description is read in conjunction with the accompanying drawings.

BRIEF DESCRIPTION OF THE DRAWINGS

FIG. 8 is a typical DGS diagram stored in a memory forming a part of the invention;

FIG. 9 is a graphical representation of typical material coefficient correction data stored in a memory forming a part of the invention;

FIG. 10 is a graphical representation of typical temperature coefficient correction data stored in a memory forming a part of the invention, and FIG. 11 is a graphical representation of the resulting compensation signal derived when the data per FIGS. 8, 9, and 10 are combined.

DETAILED DESCRIPTION OF THE INVENTION

Figure 1:
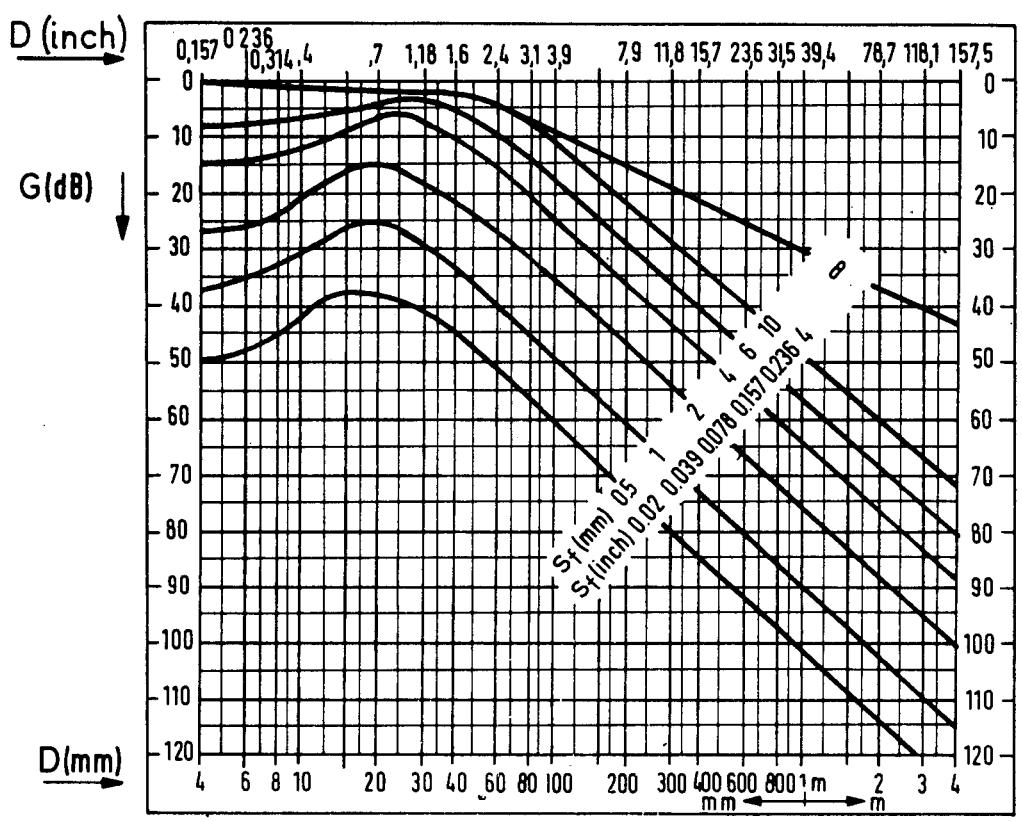
FIG. 1 is a typical DGS diagram for a test probe.
Figure 2:
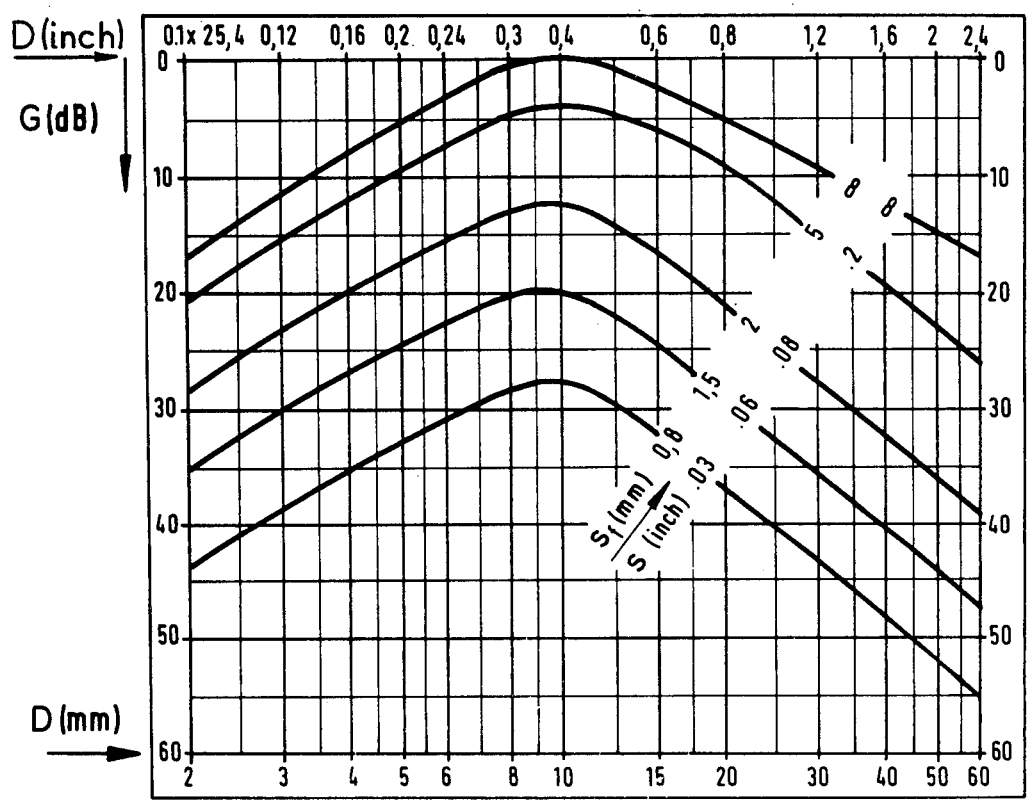
FIG. 2 is a typical DGS diagram for a transmitter/receiver test probe.

From the nature of the DGS curves shown in FIGS. 1 and 2, it is apparent that it is not possible with three-point depth compensation to ensure the same test sensitivity throughout the thickness of a workpiece without employing additional auxiliary compensation means.

Figure 3:
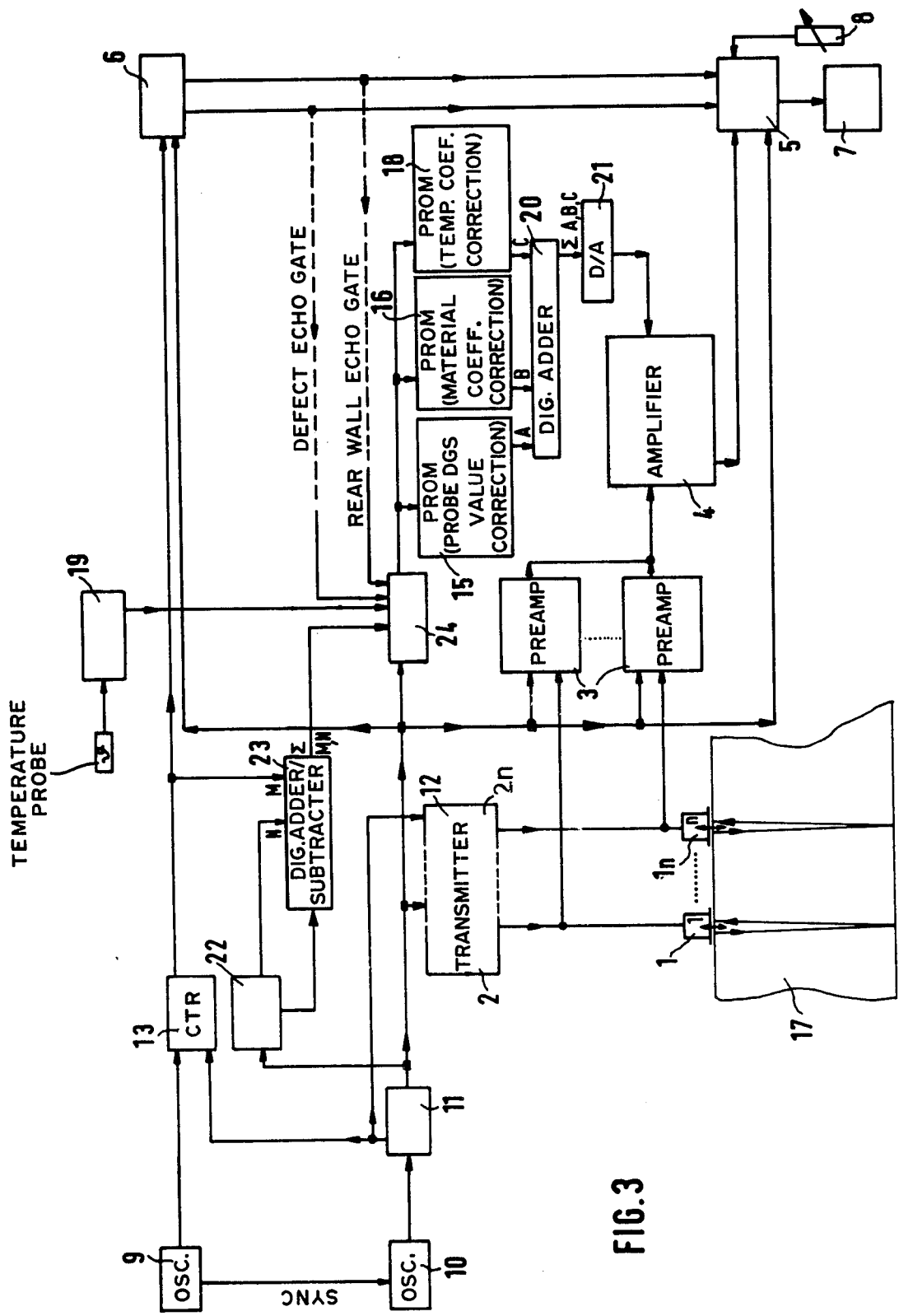
FIG. 3 is a schematic block circuit diagram of an arrangement for ultrasonic testing with automatic correction for test parameters.

FIG. 3 discloses a commonly employed arrangement for ultrasonic testing of workpieces using analog echo responsive signals. When testing, for example, sheet metal 17, an array comprising a quantity of juxtaposed test probes 1, . . . ,1n are sequentially energized by electronic switching devices. During each sequence each test probe is coupled to an associated transmitter 2 and preamplifier 3. The preamplifiers 3 are coupled by a common conductor to an amplifier 4. The amplifier 4, for instance, may be a logarithmic amplifier which is particularly suited for the present invention by achieving sensitivity (gain) compensation to provide for the correction of the DGS values, the material coefficients and the temperature coefficients. Resulting from the logarithmic measurement, it is possible to compensate the sensitivity as a function of distance by the addition of an appropriate control signal voltage, which in practice results in a better transient response.

The analog amplified echo responsive electrical signals appearing at the output of the amplifier 4 are conducted to a gate circuit 5 for evaluation. The gate circuit 5 performs an amplitude evaluation of the respective echo responsive electrical signals by furnishing an analog threshold voltage signal related to the time intervals of the defect echo gate and the rear echo wall gate as provided by the gate generator 6. At the output of the gate circuit 5 the signals, which have been evaluated as to amplitude and arranged in time in accordance with the defect echo gate and the rear wall echo gate, are available for further evaluation and analysis and for this purpose are conducted to an evaluation and indicating device 7. A further evaluation may follow, for instance, by counting and indicating the incidence of output signals exceeding or failing to reach the threshold level provided by circuit 8.

Oscillator 9 is connected to a counter 13 for providing a count of the quantity of pulses of a fixed frequency occurring after receipt of a trigger signal from ring counter 11 for identifying in digital form the workpiece depth through which the search signal is traversing. Oscillator 10, synchronized with oscillator 9, is connected to the ring counter 11 for providing trigger signals for energizing the transmitter 12 comprising a plurality of transmitters 2, . . . ,2n associated with the respective probes 1, . . . ,1n.

Figure 4:
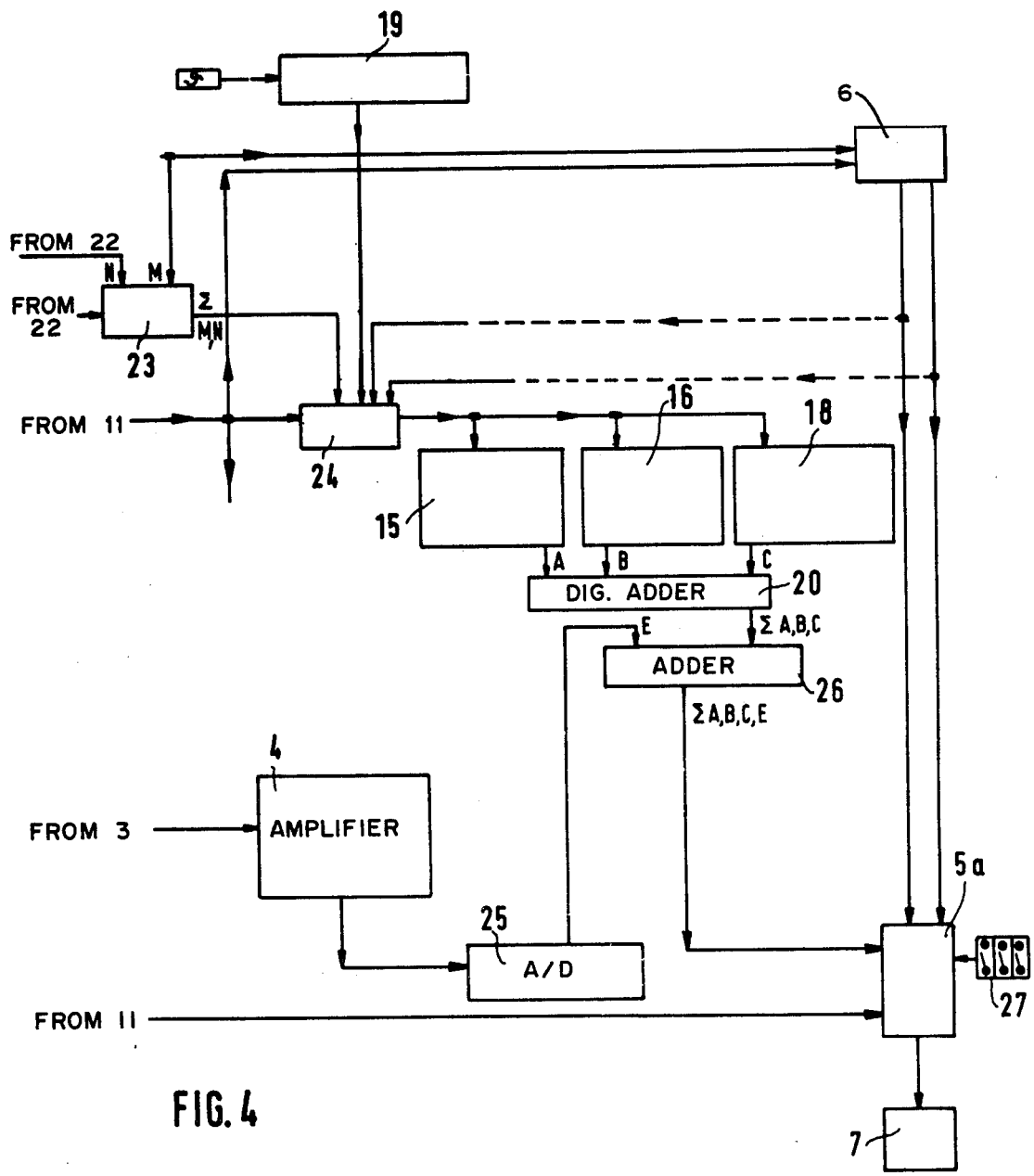
FIG. 4 is a schematic block circuit diagram showing a modification of the circuit of FIG. 3.

The modified arrangement shown in FIG. 4 provides for evaluation of echo responsive signals in digital form and has coupled, at the output of the amplifier 4, an analog to digital converter 25 from which digital echo responsive electrical signals are conducted to a digital gate circuit 5a via a digital adder 26. The digital gate circuit 5a also receives as an input a digital threshold value signal, for instance from coding switches 27. The time notation of the echo responsive signals continues to be defined by the defect gate and the rear wall echo gate generated by the gate generator circuit 6. The output of the digital gate circuit 5a is then conducted to the evaluation and indicating circuit 7.

Further explanation of the details of the invention illustrated in FIGS. 3 to 6, will now be given in relation to a preferred embodiment of a pulse-echo operation using standard test probes.

The correction of the output signals of the individual probes for the individual test parameters is carried out by continuously retrieving digitally stored data contained in previously programmed programmable read-only-memories (PROM).

In the embodiment shown in FIG. 3, a memory 15 is preprogrammed for each test probe used with data corresponding to the DGS corrections for infinitely large reflectors and for a reflector in the range of anticipated defect sizes. The entire workpiece thickness is divided up into small test regions each characterized by a digital address signal. To each test region a digitally addressable portion of the memory storage is allocated.

The digital characteristic of the workpiece test region section serves as a 'PROM address'. If necessary, for each workpiece test region, the respective relevant correction values for the material coefficients are stored in a further memory 16. In a still further memory 18 the corrections for the temperature coefficients are stored. Temperature changes affecting the test probe and the coupling medium can also be compensated for in memory 18. The address signal for the memory 18 is also provided digitally so that different temperature values across the surface of the workpiece are associated with predetermined addresses in digital form derived from the temperature probe 19. In this way different test surface temperatures of the workpiece can be included in the correction and therefore in the evaluation. The correction signals derived continuously during the transit of the search signal through the workpiece by appropriately addressing the respective memories 15, 16 and 18 are conducted to a digital adder 20. The output of this adder is coupled to a digital to analog converter 21, so that the output voltage signal of the latter is available as an analog correction voltage signal representing a correction signal related to a given test probe, workpiece thickness section, material and temperature. This correction voltage signal is provided to the amplifier 4 for affecting the gain thereof. Since test probes 1, . . . ,1n are assigned cycles 1, . . . ,n and each can exhibit different individual test probe delay distances or different coupling distances in the coupling medium, these distances are retained in a digital memory 22 (see FIG. 3) and are provided individually for the test probes 1, . . . ,1n. The absolute digital workpiece test region address signal, i.e. the quantity of pulses counted by the counter 13 corresponding to the number of pulses received from oscillator 9, and counted by counter 13 is added or subtracted in a digital addition/subtraction device 23 to the correction value applicable to the individual test probe coupling distance. This operation is done for each energizing of the respective probe. There is thus produced at the output of the addition/subtraction device 23 a corrected test region address signal compensated for the coupling distance from the test probe to the workpiece entrant surface which corrected signal is used for the actual address signal of memories 15 and 16. The oscillator 9 used for the generation of the workpiece thickness section signal oscillates in the megahertz frequency range (e.g. 30 MHz), and is phase synchronized with the oscillator 10. The oscillator 10 generates pulses at a very much lower pulse repetition frequency and triggers the ring counter 11, which in turn produces the cycles 1 . . . ,n. Simultaneously, at the start of each new cycle the common trigger signals are transmitted.

Figure 7:
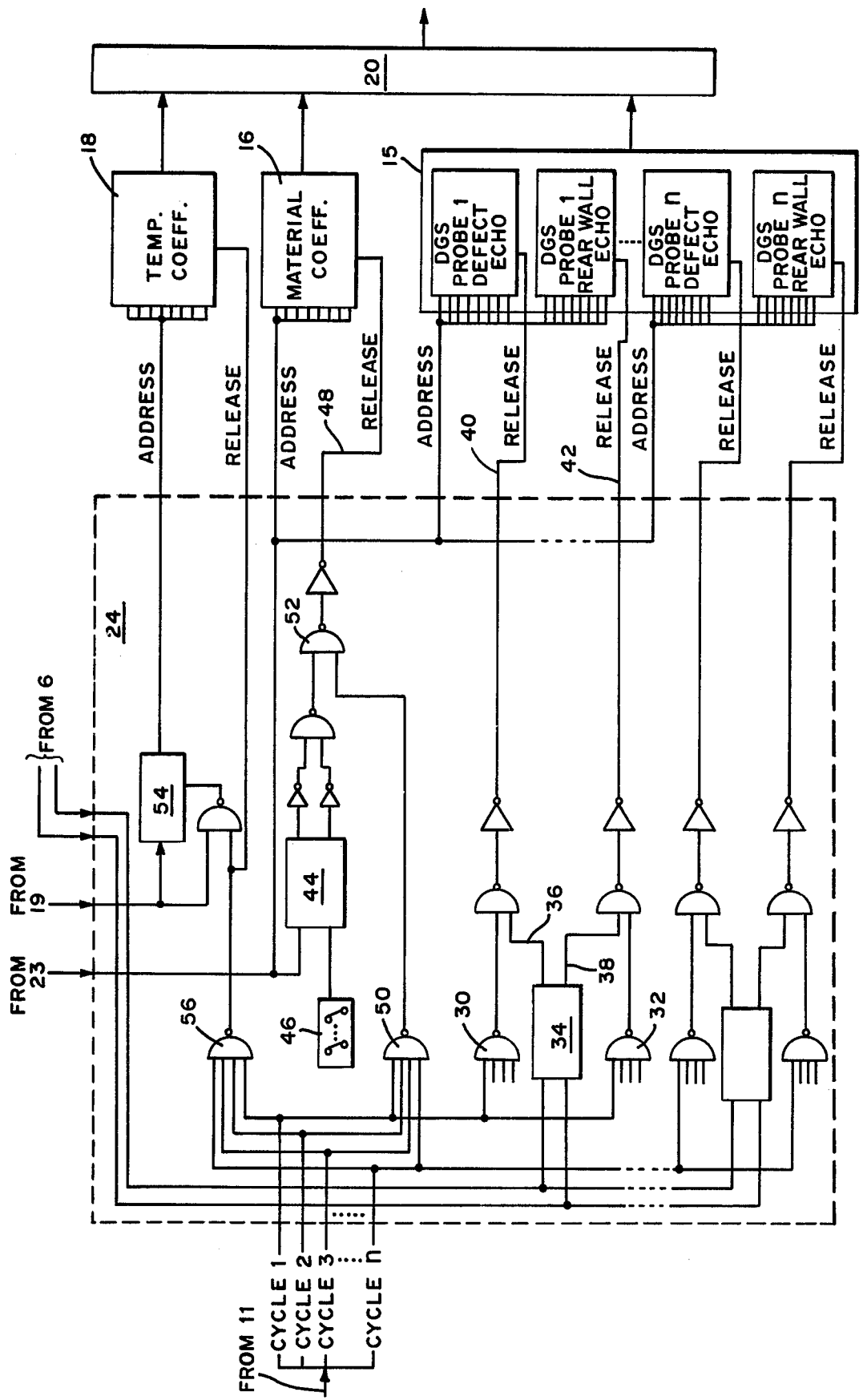
FIG. 7 is a schematic block circuit diagram of a portion of the circuit per FIGS. 3, 4, 5 and 6.

These common trigger signals are provided from ring counter 11, for instance to the ultrasonic test transmitters 2 . . . ,2n, the pre-amplifiers 3, the counter 13, the gate generator circuit 6, the gate circuit 5 and to a multiplexer 24, shown in FIG. 7, in order to synchronize the entire test system. The multiplexer 24 is designed in such a way that the value corresponding to the corrected workpiece test region address signal is properly conducted to the respective PROMs during each test cycle and that responsive to the defect echo gate or rear wall echo gate the respective memory provides the data at the correct point in time. The compensated analog echo responsive signal at the output amplifier 4 is conducted to the gate circuit 5. The threshold voltage level signal for evaluating the echo amplitude is also an analog signal and is obtained for example from a potentiometer 8. The evaluation and indicating device 7 is coupled in circuit for receiving the output signal from the gate circuit 5.

As best seen in FIG. 7, the multiplexer 24 provides the correct address signals to the respective PROMs 15, 16 and 18. During the first cycle, for instance, a trigger signal from ring counter 11 is provided to NAND gates 30 and 32. A set-reset flip-flop 34 causes a first output signal to be manifest along conductor 36 responsive to the receipt of the defect echo gate from gate generator 6 and a second output signal to be manifest along conductor 38 responsive to the receipt of the rear wall echo gate from gate generator 6. Responsive to the first output signal and the trigger signal a release signal is conducted along conductor 40 from multiplexer 24 to PROM 15 during the entire time period that the defect echo gate is present during the first cycle for causing defect correction signals to be manifest at the output of PROM 15. Responsive to the second output signal and the trigger signal a release signal is conducted along conductor 42 from multiplexer 24 to PROM 15 for causing rear wall correction signals to be manifest at the OR'd output of PROM 15.

The address signal for the PROM 15 is provided from addition/subtraction device 23 and is continuously changing responsive to the increasing count from counter 13. The continuously varying address signal to PROM 15 causes the compensation signal provided from PROM 15 to the digital adder circuit 20 to continuously change. The method of providing DGS compensation signals from PROM 15 is performed in the same manner for each of the probes 1, . . . ,1n during each respective test cycle.

A continuously varying material coefficient compensation signal from PROM 16 is also provided to the digital adder circuit 20. Upon receipt of a trigger signal from ring counter 11 at the input of NAND gate circuit 50 corresponding to any cycle 1, 2, . . . or n, a high level signal is provided to a first input of NAND gate circuit 52. Concurrently, the corrected test region address signal from addition/subtraction circuit 23 is provided to one input of a digital comparator circuit 44 and to the address input of PROM 16. The other input of digital comparator 44 is provided with a predetermined count from digital switches 46. When the corrected address signal exceeds the predetermined signal a high level signal is provided to the other input of NAND gate circuit 52. Upon the simultaneous occurrence of the high-level signals at both inputs of NAND circuit 52, a release signal is conducted from multiplexer 24 to PROM 16 via conductor 48. The material coefficient compensation signal at the output of PROM 16 continuously varies responsive to the changing address signal from addition/subtraction circuit 23 during the time that the release signal is manifest along conductor 48.

For providing temperature compensation, the signals from temperature probe 19 are fed via a D-type flip-flop 54 to the address input of PROM 18. The trigger signals from ring counter 11 are provided as inputs to NAND gate 56. Upon receipt of a trigger signal, the output of NAND gate 56 assumes its high state, providing a release signal to PROM 18. The temperature compensation signal from PROM 18 varies responsive to the temperature measured by temperature sensor 19 during each respective test cycle.

In contrast with the embodiment per FIG. 3, in the arrangement per FIG. 4 the analog echo responsive signal from the logarithmic amplifier 4 is provided to an analog to digital converter 25. The digital echo responsive signal produced at the output of the converter 25 is provided to a further adder circuit 26. The digital echo responsive signal is added to the correction signals provided from the memories 15, 16, and 18 which have previously been combined in the digital adder 20. Thus, at the output of the adder 26 there is a corrected digital echo responsive signal which is conducted to a digital echo evaluation gate circuit 5a, e.g. a digital comparator, and is compared with a predetermined digital threshold level signal provided to the gate circuit 5a via digital coding switches 27.

Figure 5:
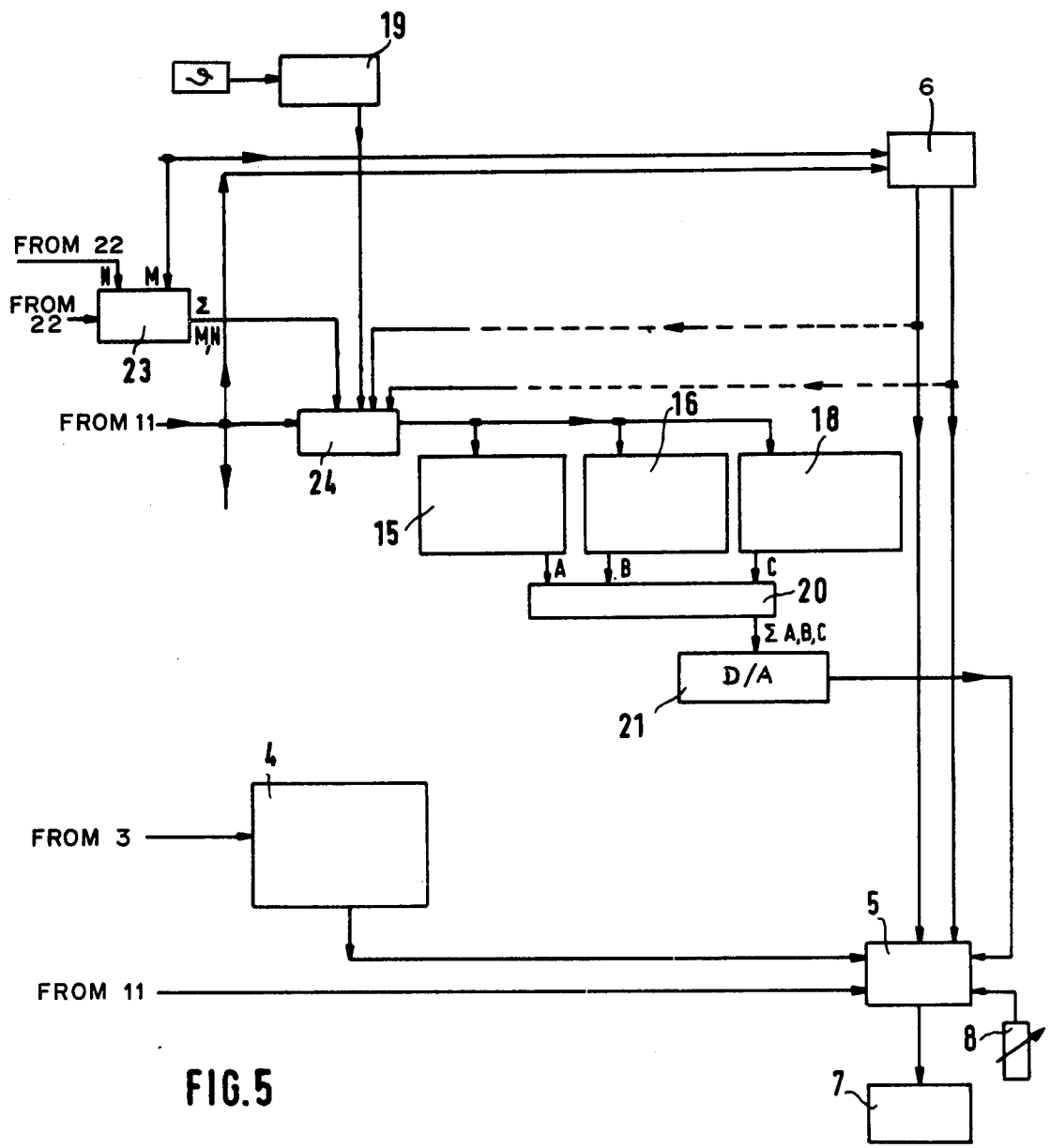
FIG. 5 is a schematic block circuit diagram showing a further modification of the circuit of FIG. 3.

FIG. 5 illustrates another embodiment of the invention using compensation signals that are derived from the memories 15, 16 and 18. The basic mode of operation of the function groups is described in accordance with the embodiments per FIGS. 3 and 4. In FIG. 5 the uncompensated echo responsive signals from the amplifier 4 are conducted to the analog echo gate circuit 5. The synchronization of the analog responsive signals occurs in proper time sequence by way of the defect echo gate and the rear wall echo gate provided from the gate generator circuit 6. The corrections provided from the memories 15, 16 and 18 are conducted via the digital adder 20 to the digital to analog converter 21 and are available at the output of the latter as analog correction signals. In contrast with the circuit of FIG. 3, this correction is not, however, used to affect the gain of the amplifier 4, but rather is used for varying the threshold level signal provided to the gate circuit 5. The initial adjustment of the threshold level signal is obtained by adjustment of the potentiometer 8, and together with the analog correction value from the digital to analog converter 21 form a resultant threshold voltage signal for the gate circuit 5.

Figure 6:
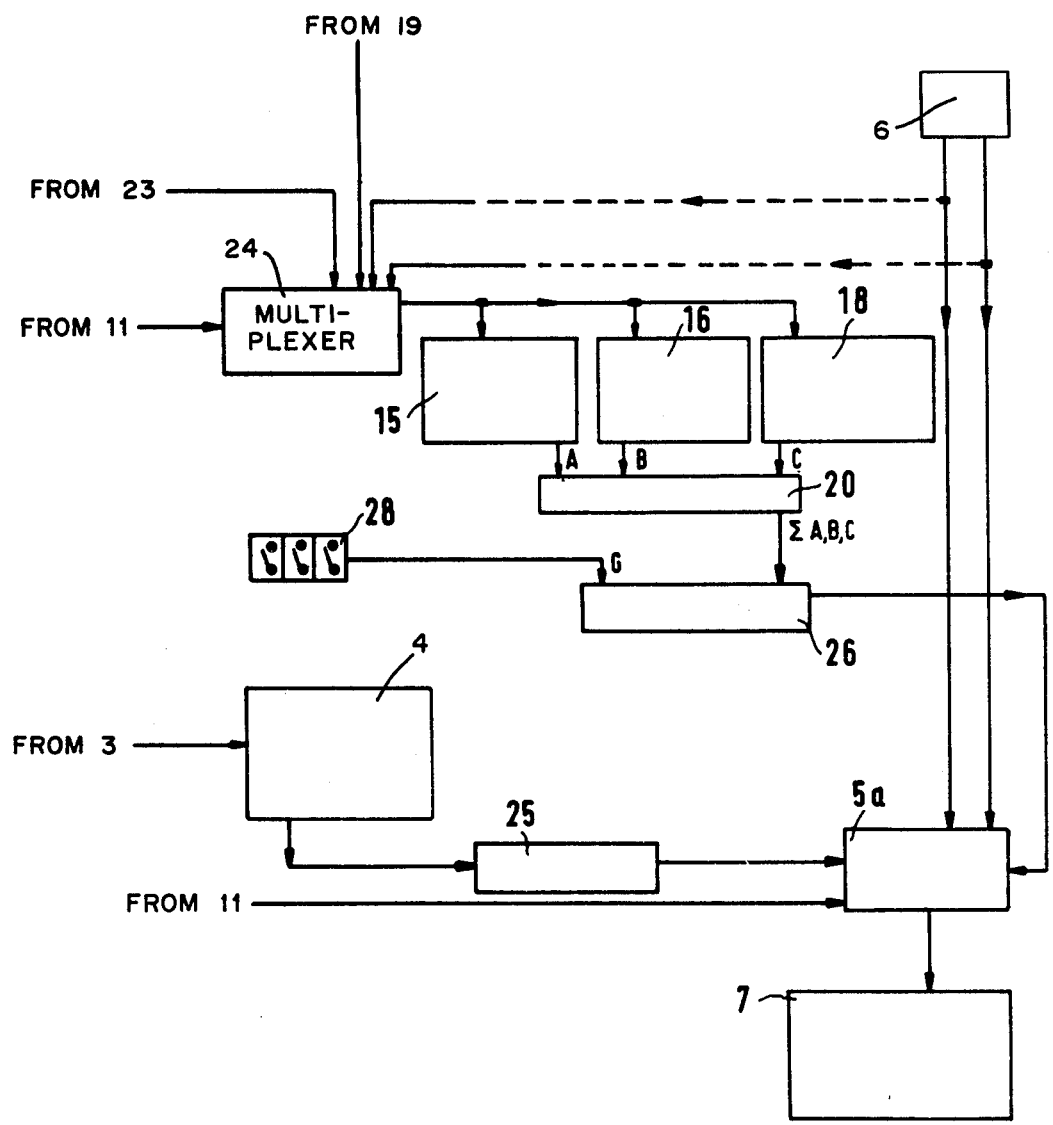
FIG. 6 is a schematic block circuit diagram of a still further modification of the circuit of FIG. 3.

FIG. 6 shows a further alternative embodiment involving corrected echo responsive signals in digital form. The output signal of amplifier 4 is conducted to the analog to digital converter 25. The converter provides the uncompensated digital echo responsive signals to the digital echo gate circuit 5a. The time identification of the echo responsive signals is derived from the defect echo gate and the rear wall echo gate produced by gate generator circuit 6. The contents of the memories 15, 16, and 18 are added in the digital adder 20 and provided as a digital sum signal to a second digital adder 26. In this second adder an initial adjustment provided from coding switches 28 is added to the sum signal from digital adder 20. The digital signal at the output of digital adder 26 provides the threshold level signal for comparing the amplitude of the uncompensated digital echo responsive signals in the digital echo gate circuit 5a with the set threshold level. The evaluation of the gate circuit 5a output signals is performed in the evaluation and indicating device 7.

FIGS. 8 through 10 show schematically typical data to be stored in the PROMs and FIG. 11 shows the sum of the stored data. FIG. 8 shows a typical DGS correction diagram applicable to a test probe.

FIG. 9 shows the material coefficient curve stored in PROM 16 and applicable to a typical workpiece which is cladded at 12 mm thickness.

FIG. 10 shows the temperature coefficient curve stored in PROM 18 applicable to temperature changes across the surface of the workpiece as measured by temperature probe 19.

FIG. 11 shows the resulting compensation curve at the output of the digital to analog converter 21, i.e., the sum of the DGS diagram correction signal, material coefficient correction signal and temperature coefficient correction signal.

The invention makes it possible to utilize any desired quantity of transducer probes and taking into account workpiece characteristics for providing simultaneous and accurately timed compensation for the test probe, material depth, coupling and temperature dependent functions. Therefore, the instant arrangements make it possible to significantly improve the accuracy of defect evaluation and automation of testing in comparison with prior apparatus known heretofore.

What is claimed is:

1. The method of testing workpieces by the ultrasonic pulse-echo method comprising:

coupling a plurality of electroacoustic transducer probe means via a coupling means to the surface of a workpiece to be tested;

storing in memory means, digitally addressed with respect to predetermined workpiece test regions, data relating to each of the probe means and data relating to the workpiece properties;

energizing said probe means for causing each of said probe means to transmit an ultrasonic search signal into the workpiece and subsequently to provide an echo responsive electrical signal arising from a respective search signal intercepting an acoustic discontinuity in the workpiece;

responsive to said probe means being energized addressing said memory means for continuously retrieving the respective probe means and workpiece properties stored data corresponding to the workpiece region traversed by the respective search signal;

combining the retrieved stored data from the memory means for forming a compensating signal;

compensating an echo responsive signal as a function of the compensating signal to derive a compensated output signal, and evaluating said compensated output signal.

2. The method of testing workpieces as set forth in claim 1, said compensating comprising applying said compensating signal as a gain control signal to an amplifier and feeding said echo responsive electrical signal to said amplifier for causing said echo responsive signal to be amplified responsive to the value of said compensating signal to derive said compensated output signal.

3. The method of testing workpieces as set forth in claim 1, said compensating comprising applying said compensating signal as a threshold level to a comparator and comparing the threshold level with the echo responsive electrical signal to derive said compensated output signal.

4. An apparatus for the ultrasonic nondestructive testing of workpieces comprising: transmitter means for periodically providing trigger signals;

a plurality of electroacoustic probe means adapted to be coupled to the surface of a workpiece coupled to said transmitter means for causing each probe means responsive to the receipt of a respective trigger signal to transmit an ultrasonic energy search signal through a coupling medium into the workpiece and to provide a respective echo responsive electrical signal responsive to said search signal intercepting an acoustic discontinuity in the workpiece;

memory means for storing digitally addressed with respect to workpiece test regions data pertaining to at least two of the following parameters, namely DGS values associated with individual ones of said probe means, workpiece properties, and coupling medium characteristics;

address means coupled to said transmitter means for providing responsive to each said respective trigger signal an address signal commensurate with the test region in the workpiece through which said search signal is traversing;

multiplexer means coupled to said address means and said memory means for receiving said address signal and selectively providing said address signal to a respective said memory means to cause said stored data to be manifest as a continuously updated data signal corresponding to said parameters from said memory means;

summing means coupled to said memory means for receiving said data signals and combining said data signals to form a compensating signal, and evaluation means coupled to said probe means and said summing means for receiving said echo responsive electrical signal and said compensating signal commensurate with the test region from which said echo responsive signal arises for providing compensation of said echo responsive electrical signal as a function of said compensating signal.

5. An apparatus as set forth in claim 4, said evaluation means comprising:

amplifier means coupled to said probe means for receiving and amplifying said echo responsive electrical signal, and comparator means coupled to said amplifier means for receiving said amplified echo responsive electrical signal and comparing the amplitude of said amplified echo responsive electrical signal with a threshold level.

6. An apparatus as set forth in claim 5, the gain of said amplifier means being varied responsive to said compensating signal.

7. An apparatus for the ultrasonic nondestructive testing of workpieces comprising:

transmitter means for periodically providing trigger signals;

a plurality of electroacoustic probe means adapted to be coupled to the surface of a workpiece coupled to said transmitter means for causing each probe means responsive to the receipt of a respective trigger signal to transmit an ultrasonic energy search signal through a coupling medium into the workpiece and to provide a respective echo responsive electrical signal responsive to said search signal intercepting an acoustic discontinuity in the workpiece;

memory means for storing digitally addressed with respect to workpiece test regions data pertaining to at least two of the following parameters, namely DGS values associated with individual ones of said probe means, workpiece properties, and coupling medium characteristics;

address means coupled to said transmitter means and said memory means for providing responsive to said trigger signal an address signal to said memory means commensurate with the test region in the workpiece through which said search signal is traversing to cause said stored data to be manifest as a continuously updated compensating signal from said memory means;

amplifier means coupled to said probe means for receiving and amplifying said echo responsive electrical signal, and comparator means coupled to said amplifier means and said memory means for receiving said amplified echo responsive electrical signal and comparing the amplitude of said amplified echo responsive electrical signal with a threshold level which varies as a function of said compensating signal.

8. An apparatus for the ultrasonic nondestructive testing of workpieces comprising:

transmitter means for periodically providing trigger signals;

a plurality of electroacoustic probe means adapted to be coupled to the surface of a workpiece coupled to said transmitter means for causing each probe means responsive to the receipt of a respective trigger signal to transmit an ultrasonic energy search signal through a coupling medium into the workpiece and to provide a respective echo responsive electrical signal responsive to said search signal intercepting an acoustic discontinuity in the workpiece;

memory means for storing digitally addressed with respect to workpiece test regions data pertaining to at least two of the following parameters, namely, DGS values associated with individual ones of said probe means, workpiece properties, and coupling medium characteristics;

oscillator means for providing pulses at a high repetition frequency;

means for storing coupled to said transmitter means for providing responsive to said trigger signal a value corresponding to a coupling distance and coupling medium associated with an individual said probe means;

addition/subtraction means coupled to said oscillator means and said means for storing for providing a distance corrected signal;

gate generating means coupled to said oscillator means and said transmitter means for providing responsive to said trigger signal a defect echo gate during the time interval in which the receipt of defect responsive echo signals is anticipated and a rear wall echo gate during the time interval in which the receipt of a rear wall echo signal is anticipated;

multiplexer means coupled to said addition/subtraction means, said gate generating means, said transmitter means and said memory means for providing to said memory means an address signal commensurate with the workpiece test region through which said search signal is traversing and the individual said probe means associated with said search signal to cause said stored data to be manifest as a continuously updated compensating signal from said memory means, and evaluation means coupled to said probe means and said memory means for receiving said echo responsive electrical signal and said compensating signal commensurate with the test region from which said echo responsive signal arises for providing compensation of said echo responsive electrical signal as a function of said compensating signal.

9. An apparatus as set forth in claim 4, including additonal memory means for storing digitally addressed with respect to temperature data pertaining to the temperature of the workpiece, and temperature sensing means coupled for providing a temperature signal commensurate with the workpiece temperature to said multiplexer means, and said multiplexer means providing responsive to said temperature signal an address signal to said memory means for storing digitally addressed with respect to temperature data commensurate with such workpiece temperature whereby to cause the stored data to be manifest as an additional data signal to said summing means.

10. An apparatus for the ultrasonic nondestructive testing of workpieces comprising:

transmitter means for providing a sequentially timed trigger signal;

a plurality of electroacoustic probe means adapted to be coupled to the surface of a workpiece coupled to said transmitter means for causing each probe means responsive to the receipt of a respective trigger signal to transmit an ultrasonic energy search signal through a coupling medium into the workpiece and to provide a respective echo responsive electrical signal responsive to the associated search signal intercepting an acoustic discontinuity in the workpiece;

memory means for storing digitally addressed with respect to workpiece thickness regions data pertaining to at least two of the following parameters, namely, DGS values associated with each of said probe means, workpiece properties, and coupling medium characteristics;

address means coupled to said transmitter means for providing responsive to said trigger signal being coupled to a respective probe means an address signal commensurate with the thickness region in the workpiece through which the search signal associated with said respective probe means is traversing;

multiplexer means coupled to said address means and said memory means for receiving said address signal and selectively providing said address signal to a respective said memory means to cause said stored data to be manifest as a continuously updated data signal corresponding to said parameters from said memory means;

summing means coupled to said memory means for receiving said data signals and combining said data signals to form a compensating signal, and evaluation means coupled to said probe means and said summing means for receiving said echo responsive electrical signal and said compensating signal commensurate with the thickness region from which said echo responsive signal arises for providing compensation of said echo responsive electrical signal as a function of said compensating signal.

11. An apparatus as set forth in claim 10, including additional memory means for storing digitally addressed with respect to temperature data pertaining to the temperature of the workpiece, and temperature sensing means coupled for providing a temperature signal commensurate with the workpiece temperature to said multiplexer means, and said multiplexer means providing responsive to said temperature signal an address signal to said memory means for storing digitally addressed with respect to temperature data commensurate with such workpiece temperature whereby to cause the stored data to be manifest as an additional data signal to said summing means.

* * * * *